United States Patent [19]

Hart et al.

[11] Patent Number: 5,385,553
[45] Date of Patent: Jan. 31, 1995

[54] TROCAR WITH FLOATING SEPTUM SEAL

[75] Inventors: Charles C. Hart, Huntington Beach; Mark A. Ritchart, Murietta; Donald L. Gadberry, San Juan Capistrano, all of Calif.

[73] Assignee: Applied Medical Resources Corporation, Laguna Hills, Calif.

[21] Appl. No.: 77,005

[22] Filed: Jun. 15, 1993

Related U.S. Application Data

[63] Continuation-in-part of Ser. No. 952,300, Sep. 28, 1992, Pat. No. 4,308,336, which is a continuation-in-part of Ser. No. 732,141, Jul. 18, 1991, Pat. No. 5,209,737.

[51] Int. Cl.⁶ ............................................ A61M 39/04
[52] U.S. Cl. .................................... 604/167; 604/256
[58] Field of Search ................................ 604/167, 256

[56] References Cited

U.S. PATENT DOCUMENTS

| | | |
|---|---|---|
| 3,853,127 | 12/1974 | Spademan . |
| 3,994,287 | 11/1976 | Turp . |
| 4,240,411 | 12/1980 | Hosono . |
| 4,430,081 | 2/1984 | Timmermans . |
| 4,673,393 | 6/1987 | Suzuki . |
| 4,715,360 | 12/1987 | Akui et al. . |
| 4,723,550 | 2/1988 | Bales . |
| 4,758,225 | 7/1988 | Cox et al. ............... 604/126 |
| 4,842,591 | 6/1989 | Luther ..................... 604/167 |
| 4,857,062 | 8/1989 | Russell . |
| 4,909,798 | 3/1990 | Fleischhacker . |
| 4,917,668 | 4/1990 | Haindl ..................... 604/167 |
| 4,929,235 | 5/1990 | Merry et al. ........... 604/167 |
| 4,960,412 | 10/1990 | Fink ........................ 604/167 |
| 4,966,588 | 10/1990 | Rayman . |
| 5,104,383 | 4/1992 | Schichman . |
| 5,127,626 | 7/1992 | Hilal et al. ............. 604/167 |
| 5,180,373 | 1/1993 | Green et al. ........... 604/167 |
| 5,197,955 | 3/1993 | Stephens et al. ...... 604/167 |
| 5,209,737 | 5/1993 | Ritchart et al. ....... 604/256 |

*Primary Examiner*—Paul J. Hirsch
*Attorney, Agent, or Firm*—Richard L. Myers

[57] ABSTRACT

A trocar having a cannula and housing which define an access channel, is configured to receive a surgical instrument. A flexible valve disposed in the channel includes first portions which define an orifice through the valve and second portions which are disposed outwardly of the first portions. The second portions are provided with a greater flexibility so that when the instrument is inserted off-axis, the second portions of the valve will deform before the first portions causing the orifice to move without substantial deformation to the off-axis location. Alternatively, levers engaging the first portions of the valve can be pivotally mounted on a floating ring to move the substantially undeformed orifice to the off-axis location. An associated method includes the steps of deforming the second portions of the valve without substantially deforming the first portions of the valve to move the orifice into axial alignment with the instrument.

25 Claims, 6 Drawing Sheets

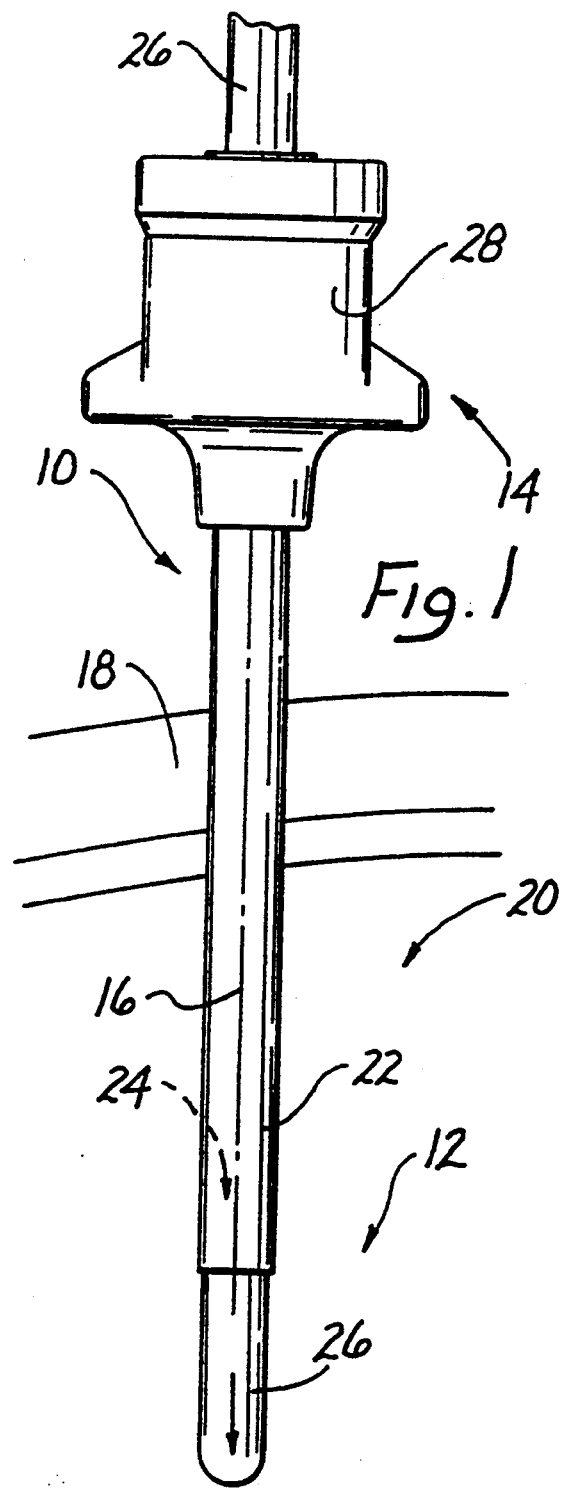

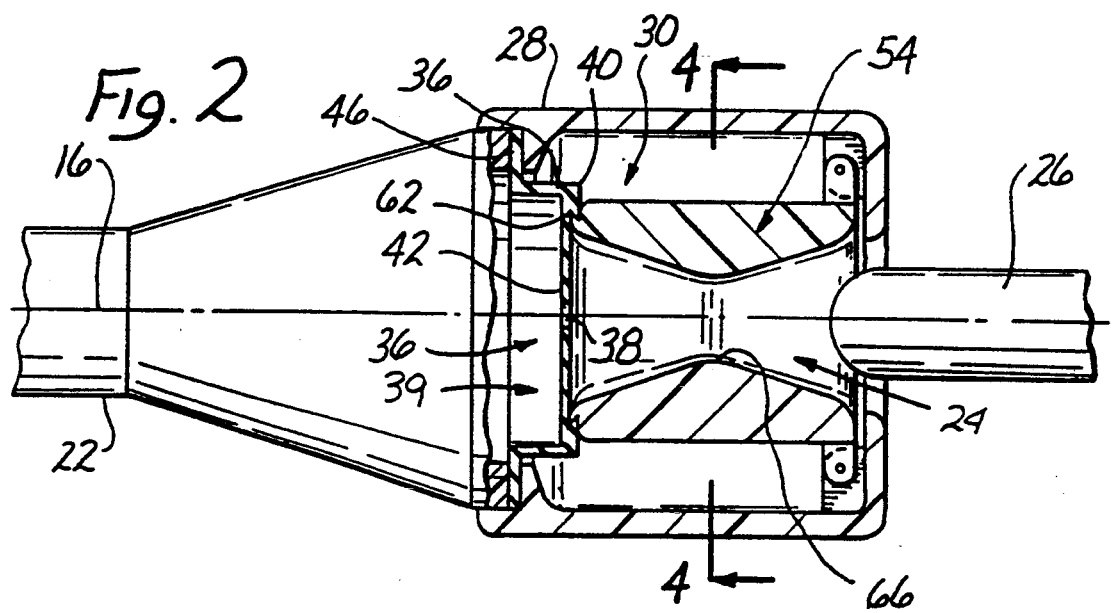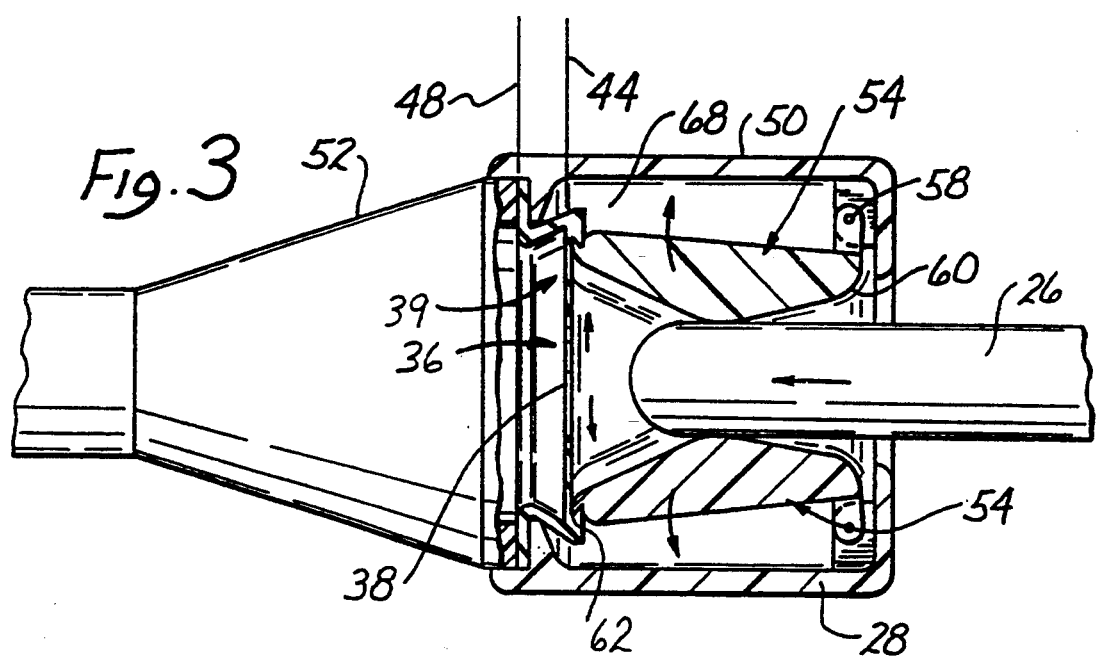

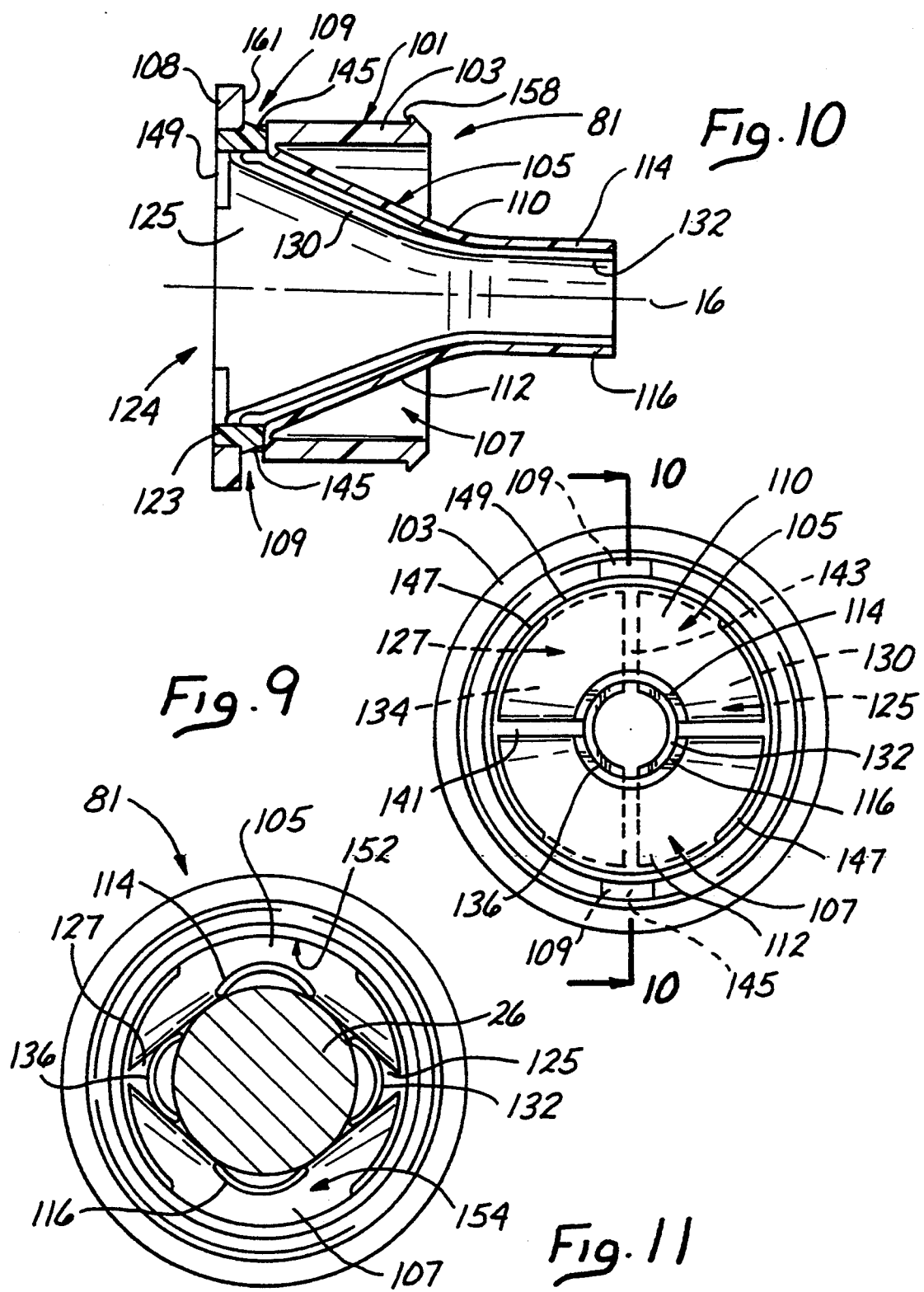

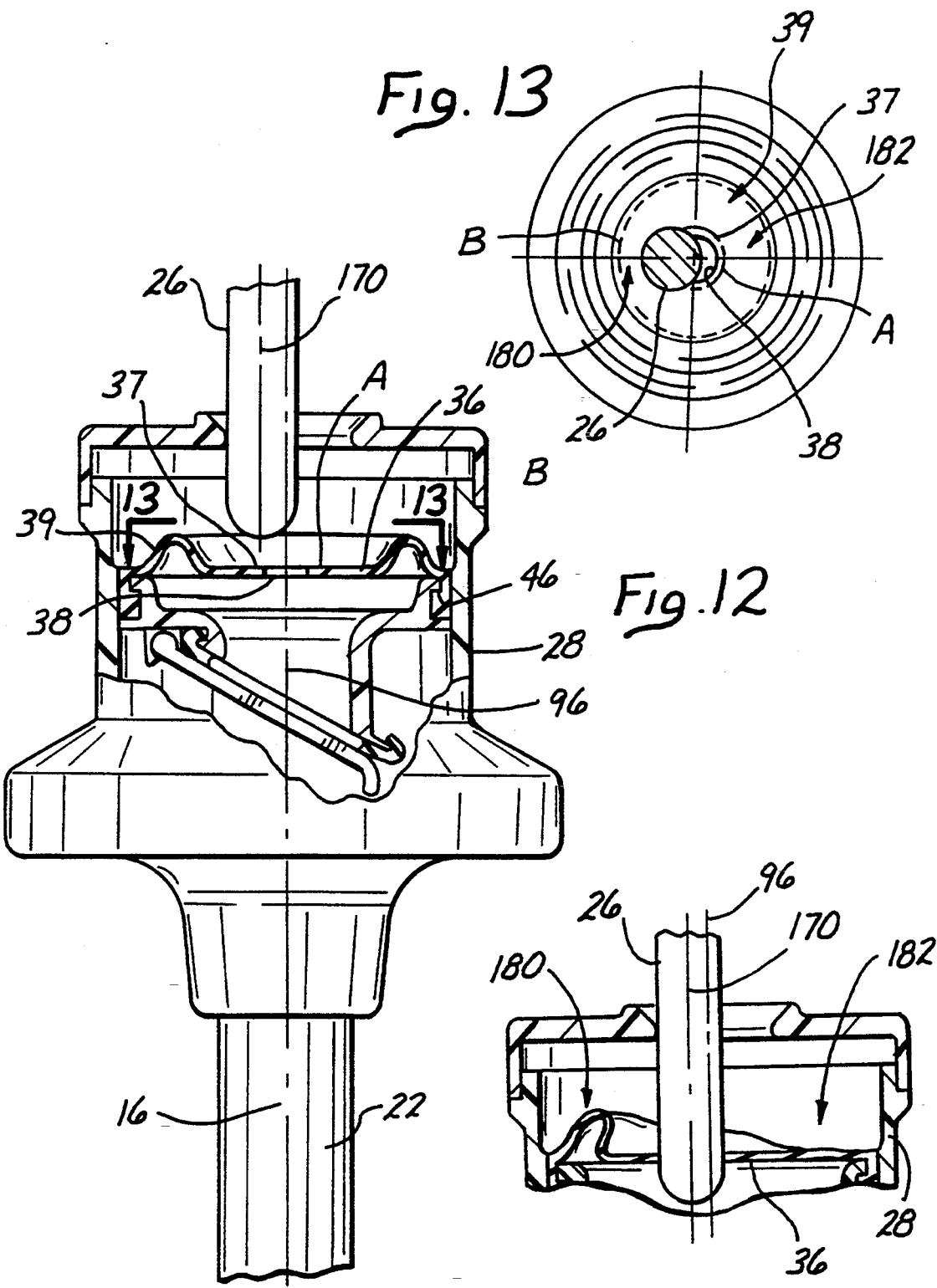

TROCAR WITH FLOATING SEPTUM SEAL

CROSS-REFERENCE TO RELATED APPLICATIONS

This application is a continuation-in-part of U.S. Pat. application Ser. No. 07/952,300 filed Sep. 28, 1992 now U.S. Pat. No. 4,308,336 and entitled Seal Protection Mechanism, which is a continuation-in-part of Ser. No. 07/732,141, filed Jul. 18, 1991, of U.S. Pat. No. 5,209,737 issued May 11, 1993 and entitled Lever Actuated Septum Seal.

BACKGROUND OF THE INVENTION

1. Field of the Invention

This invention relates generally to access devices, such as trocars, and more specifically to access devices including at least one septum valve.

2. Discussion of the Prior Art

Laparoscopic surgery is conducted through trocars which extend across the abdominal wall and provide channels through which instruments such as scopes, retractors and staplers can be inserted to perform surgery in the abdominal cavity. As a part of this procedure, the abdomen is inflated with an insufflation gas to maintain the abdomen in a distended state. Valves are typically provided in the trocars to form seals around the instruments in order to prevent leakage of this insufflation gas. A variable as it is able to conform to any size of instrument, regardless of its diameter, without increasing the friction or drag on the instrument. A variable diameter septum valve of this nature is disclosed and claimed by applicant in the parent application Ser. No. 07/732,141, filed on Jul. 18, 1992 and entitled Lever Actuated Septum Seal.

Variable diameter seals have a high degree of compliance which is of particular advantage in accommodating different sizes of instruments. However, this compliance can present a problem if a particular instrument is bifurcated or is inserted off center. Under these circumstances, the sharp point of the instrument can localize forces along the side of the valve providing undesirable cupping and perhaps tearing of the seal. This can occur with any septum seal, although the highly compliant variable diameter seals appear to be most susceptible to damage.

The off-axis insertion of an instrument can also be a problem once the instrument extends through the orifice of the septum valve. If this orifice is pulled off-axis, it tends to develop a "cat-eye" which degrades the seal around the instrument and permits for undesirable leakage.

SUMMARY OF THE INVENTION

In accordance with the present invention, a protection mechanism has the configuration of a funnel extending along the axis of the trocar. In one embodiment, this mechanism engages the instrument in an extended position but is movable with the instrument distally axially into close proximity with the septum valve. In this distal position, the mechanism extends between the instrument and at least the outer portions of the seal. In a preferred embodiment, the mechanism actually extends through an aperture in the seal as the instrument passes through an aperture. When forward pressure on the instrument ceases, the elastomeric characteristics of the seal radially compress the protection mechanism and tend to move it rearwardly to its initial proximal position. This movement can be assisted by a slight withdrawal of the instrument if necessary. With the protection mechanism disposed in the proximal position, the septum valve is free to form a seal with the instrument.

The present invention also includes the concept of a floating septum seal which provides for movement of the septum orifice to an off-axis position without deformation. Thus the inner portions which define the orifice are moved substantially intact so that the orifice does not change from its circular configuration as it moves laterally to accommodate the off-axis insertion of an instrument. In one embodiment, the septum valve is formed with outer portions having a reduced resiliency compared to the that of the inner portions which define the orifice. This encourages the outer portions to deform first pulling the inner portions substantially undeformed to an off-axis position.

In another embodiment, lever actuators are pivotally mounted on a ring which floats in an enlarged annular recess. When an instrument is inserted off-axis, the lateral force on the levers moves the inner portions of the valve laterally but undeformed as the outer portions are stretched.

In one aspect of the invention, a trocar is adapted to form an access channel across a body wall and configured to receive a surgical instrument. The trocar includes a cannula having an axis with a seal housing disposed at the distal end of the cannula and defining with the cannula the access channel. A flexible valve is disposed across the access channel and provided with elastomeric properties for forming a seal with the instrument. First portions of the valve define an orifice which is normally concentric with the axis of the cannula. Second portions of the valve disposed circumferentially outwardly of the first portions facilitate movement of the orifice from a first position generally concentric with the axis of the cannula to a second position generally removed from the axis of the cannula in response to insertion of the instrument along a line removed from the axis of the cannula.

In an additional aspect of the invention, the housing of the trocar defines an annular recess with a first diameter. A ring, disposed in this recess, has a second diameter and supports a plurality of levers which extend to engage the valve in proximity to the orifice. The second radius of the ring is less than the first radius of the annular recess so that the ring and levers are free to float radially of the axis of the cannula. As a result, movement of the ring and levers cause the orifice to move from the axis of the cannula without substantial deformation.

A further aspect of the invention includes a method for forming a seal around an instrument introduced off-axis through an access device. The method includes the steps of providing a valve in the access device, the valve having an axis and including first portions defining an aperture sized and configured to receive the instrument. Second portions of the valve are disposed outwardly of the first portions and have a greater flexibility than the first portions. The instrument is inserted into the access device and brought into contact with the valve at a location off-axis relative to the aperture. Pushing the instrument into the aperture forms a seal between the valve and the instrument. During the pushing step, the second portions of the valve are deformed without substantially deforming the first portions of the valve so that the aperture moves off-axis into axial alignment with the instrument.

These and other features and advantages of the invention will be more apparent with a discussion of preferred embodiments and the best mode of the invention, taken in combination with the associated drawings.

DESCRIPTION OF THE DRAWING

FIG. 1 is a side elevation of a trocar assembly operatively positioned to penetrate a tissue barrier;

FIG. 2 is an axial cross-section view of the trocar, showing details of a variable diameter septum valve assembly prior to insertion of a surgical instrument therein;

FIG. 3 is an axial cross-section view similar to that of FIG. 2, showing details of the same embodiment of the trocar valve assembly during insertion of the surgical instrument;

FIG. 9 is an end view of one embodiment of the seal protection mechanism;

FIG. 10 is an axial cross-section view of the seal protection mechanism of FIG. 9;

FIG. 11 is an end view of the seal protection mechanism similar to FIG. 10 but illustrating an instrument extending through the mechanism as illustrated in FIG. 8;

FIG. 12 is a side-view partially in phantom of the trocar and a floating septum valve of the present invention;

FIG. 13 is a radial view taken along lines 13—13 of FIG. 12; and

FIG. 14 is a radial cross-section view similar to FIG. 12 and illustrating the septum valve with its undeformed orifice displaced off-axis.

DESCRIPTION OF PREFERRED EMBODIMENT AND BEST MODE OF THE INVENTION

Figure 4:
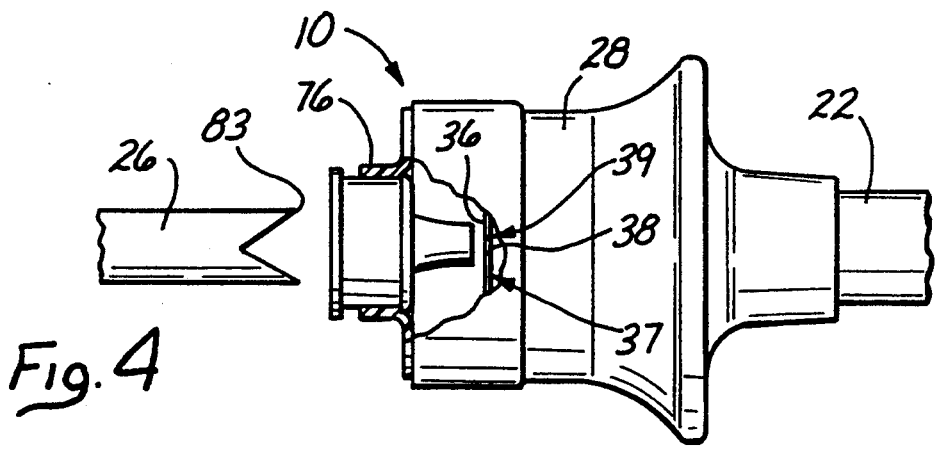
FIG. 4 is a side elevation view of a trocar extending across the abdominal wall and including one embodiment of a seal protection mechanism of the present invention.

A surgical trocar is illustrated in FIG. 1 and designated generally by the reference numeral 10. The trocar 10 is representative of any elongate access device having a distal end 12 and a proximal end 14. It is typically configured along a longitudinal axis 16 and is generally circular in radial cross-section.

It is the purpose of the trocar 10 to form a channel through a tissue barrier in order to provide access across the barrier into a body cavity. By way of example, the tissue barrier may include an abdominal wall 18 which defines an abdominal cavity 20. The trocar 10 typically includes an elongate tube or cannula 22 having a cylindrical configuration and a wall thickness which may be on the order of 0.015 or 0.030 inches. The cannula 22 has an interior bore or channel 24 which may have a diameter in a range between 5 and 12 millimeters. The trocar 10 is designed to pierce, cut, incise, or otherwise puncture the tissue barrier, such as the abdominal wall 18, and to leave the cannula 22 extending through the incision. An elongate surgical instrument 26 is representative of various cutters, clamps, traction devices, visualization devices, aspirators and irrigators as well as other types of instrument, which have different diameters. In operation, the instrument 26 is positioned through the channel 24 of the trocar 10 and manipulated to perform a particular surgical procedure within the cavity 20.

The trocar 10 includes a valve housing 28 which encloses a valve mechanism 30 such as that shown in FIGS. 2–4. These figures illustrate the trocar 10 at a point in time after it has been inserted through the abdominal wall 18 leaving the cannula 22 to provide access to the abdominal cavity 20.

The valving mechanism 30 includes a septum valve 36, which is preferably molded from an elastomeric material such as C-flex ®, a low durometer polymer manufactured by Concept Polymer Technologies. This material is chosen for its high degree of compliance which makes it particularly adaptable to instruments having different diameters. Of course, other known elastomeric materials could be used instead to accomplish the objectives of the invention.

The valve 36, which is characterized as a septum valve, is deemed to include any valve which has properties for radially compressing against the outer surface of an instrument, such as the instrument 26. Included in this definition without limitation is the valve disclosed and claimed in applicant's U.S. Pat. No. 5,127,626, issued on Jul. 7, 1992, and entitled Apparatus for Sealing Around Members Extending Therethrough, which is incorporated herein by reference.

The septum valve 36 includes inner portions 37 which define a central orifice or aperture 38 that is preferably centered about the axis 16 of the trocar 10. The aperture 38 in a relaxed state has a cross-sectional area which, in one embodiment may be substantially zero, and in a different embodiment may be small, but greater than zero. The septum valve 36 also includes outer portions 39 which extend radially outwardly from the inner portions 37.

In the illustrated embodiment, the septum valve 36 also includes an annular flange or lip 40 which is preferably concentric with the aperture 38 and may be disposed in either the inner portions 37 or outer portions 39. The septum valve 36 in the illustrated embodiment also includes seating portions 46 which are clamped between the valve housing 28 and a transition housing 52.

A plurality of levers 54 are disposed outwardly of the elongate axis 16, in such a manner as to define a continuation of the channel 24. In a preferred embodiment, four such levers 54 are provided, but any number of levers could be employed, with suitable modifications in design.

Each lever 54 can be mounted on a pivot 58 at its proximal end 60, with the pivotal axis being transverse to the elongate axis 16. At least one tooth member 62 can be provided at a distal end 64 of each lever 54. This tooth member 62 is adapted to engage and interlock with the lip 40. In the illustrated embodiment, the lever teeth 62 collectively form a substantially circular tooth member which engages the circular lip 40 about it circumference. Between the pivot point 58 and the tooth member 62, each of the levers 54 extends radially inwardly to define a throat 66 of the channel 24. An open space 68 lies radially outwardly of both the levers 54 and the annular flange or lip 40, within the valve housing 28. This space 68 accommodates outward expansion of the levers 54 and the septum valve 36.

In operation, it may be desired to insert the surgical instrument 26 through the channel 24 and into the body cavity 18. To do so, the instrument 26 is first inserted into the valve housing 28 as shown in FIG. 3. The instrument 26 has a particular cross-sectional diameter which may vary according to the type of instrument, but it must be greater than the radial distance separating the levers 54 in order for the levers 54 to be actuated.

As the instrument 26 is pushed into the throat 66 of the channel 24, it pushes the levers 54 radially outwardly, thereby rotating the levers about their respective pivots 58. This moves the tooth members 62 of the lever 54 radially outwardly, as shown by the arrows 67 in FIG. 3. The engaging relationship between the lever teeth 62 and the lip 40 expands the lip radially outwardly thereby expanding the diameter of the aperture 38.

The leverage provided by the levers 54 is best illustrated again by reference to FIG. 3, where it can be seen that the lever arm for measuring the diameter of the instrument 26 is less than the lever arm for spreading the lip 40. The expansion of the lip 40 in turn stretches the septum 36, causing the radial width of the aperture 38 to be expanded, as shown by the arrows 67. The aperture is preferably expanded to a cross-sectional diameter which is slightly smaller than the cross-sectional diameter of the instrument 26. This will enable the instrument 26 to pass easily through the aperture 8 while the valve 36 engages the instrument with a force sufficient to create a seal. With the valve 36 prestressed by the levers 54, this sealing force will not create significant frictional resistance between the instrument 26 and the septum 38. Such resistance is to be avoided since it not only opposes forward movement of the instrument 26, but also tends to tear the valve 38.

Of particular interest to the present invention is an embodiment illustrated in FIG. 4 wherein the trocar 10 is provided with a proximal end cap 74 which can be held in a snap fit relationship with the valve housing 28. This end cap 74 includes an annular flange 76 which extends axially proximally of the trocar 10. This flange 76 is adapted to receive a seal protector 81 which is of particular interest to the present invention.

The protector 81 is movable axially within the flange 76 between a proximal position illustrated in FIG. 4 and a distal position discussed in greater detail below. This protector 81 is particularly advantageous when the trocar 10 is used in conjunction with an instrument 26 having sharp points at its distal tip. Such an instrument 26 might include a clip applier having a bifurcated distal end with pointed tips 83.

Figure 5:
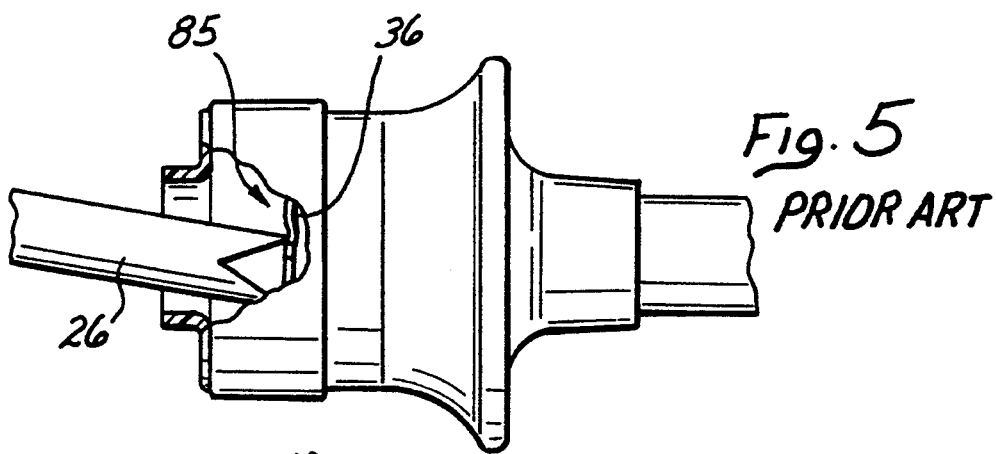
FIG. 5 is a side elevation view of a trocar of the prior art illustrating a cupping problem associated with some instruments.

Use of such an instrument 26 with previous trocars has been particularly damaging to the septum valves of the prior art as can be appreciated with reference to FIG. 5. When instruments having pointed tips have been inserted into the trocars of the prior art, the tips have sometimes engaged the septum valve outwardly from the central orifice or aperture. Preferably, the valve would spread radially under these conditions so that the instrument would eventually pass through the central aperture. However, in some cases, the valve 36 has been formed from sufficiently compliant material that it has tended to form a cup such as that shown generally at 85 in FIG. 5. When this happens, the localized pressure caused by the insertion forces has typically punctured or torn the septum 36.

Although cupping is most commonly associated with instrument having bifurcated tips, the problem can occur with any type of instrument having a pointed tip. Also, cupping can result with any type of septum valve although the highly compliant variable diameter valves, such as valve 36, previously discussed appear to be most susceptible.

It is the purpose of the seal protector 81 to isolate the outer portions 39 of the septum valve 36 from damaging contact with a pointed instrument tip, such as the tip 83. For the purposes of this discussion the inner portions 37 and outer portions 39 of the valve 36 are separated based on the response of a particular valve 36 to a pointed tip 83. If the tip 83 contacts the valve 36 at a point on the valve 36 where cupping would occur, this point is deemed to be within the outer portions 39. In contradistinction, if the pointed tip 83 of an instrument 26 contacts the valve 36 at a point on the valve which would not produce cupping, that point is deemed to be within the inner portions 37. Thus the inner portions 37 and outer portions 39 will vary for different septum valves 36 depending upon the shape and material of the valve 36 as well as the configuration of the tip 83 of the instrument 26. The compliance of the material forming the valve will be a primary consideration, but other physical characteristics of the valve 36 may also contribute to cupping at a particular point on the valve 36.

Figure 6:
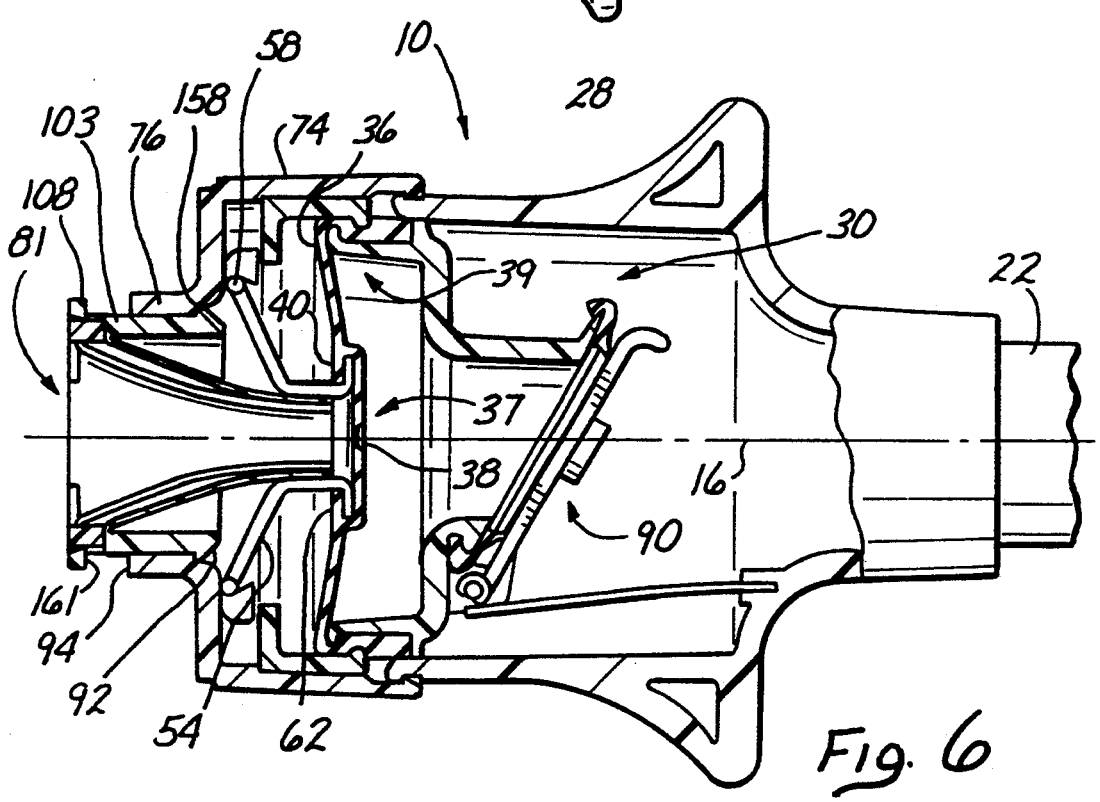
FIG. 6 is an axial cross-section view of a trocar and a further embodiment of the seal protection mechanism of the present invention.

The invention is illustrated in greater detail in FIG. 6 which differs from previously described embodiments in several respects. In the embodiment of FIG. 6, the valving mechanism 30 includes not only the septum valve 36 but also a flapper valve 90 which is of no particular interest to the present invention. Although the levers 54 are illustrated to have a more narrow configuration, they still rotate on the pivots 58 and include the tooth members 62. The septum valve 36 has a different configuration, but it also extends across the channel 24 and includes the inner portions 37 which define the aperture 38 and the outer portions 39 which form a seal with the housing 28. In this detailed view of FIG. 6, it is apparent that the annular flange 76 of the end cap 74 includes an inner shoulder and an outer surface 94.

The seal protector 81, which is mounted on the trocar 10 in FIG. 6, is shown in an enlarged isolated view in FIG. 10. This enlarged view illustrates an embodiment, wherein the seal protector 81 is formed in two sections. A distal section 101 has an outer cylinder 103 and a pair of integral outer leaves 105 and 107. The distal section 101 also includes an integral annular flange 108 which extends radially outwardly and defines with the cylinder 103 a pair of windows 109. The outer leaves 105 and 107 include funnel portions 110 and 112, respectively, which extend radially distally inwardly from the cylinder 103. The leaves 105 and 107 also include distal portions 114 and 116, respectfully, which may also have the configuration of a cylinder.

A proximal section 121 of the seal protector 81 also includes an outer cylinder 123 and a pair of integral inner leaves 125 and 127 (FIG. 9). These leaves 125 and 127 are configured similar to the leaves 105 and 107. Thus the inner leaf 125 includes a funnel section 130 and a distal section 132 while the inner leaf 127 includes a funnel section 134 and a distal section 136. These two sections of the seal protector 81, the distal section 101 and the proximal section 121, are intended to be disposed in fixed relationship with the inner leaves 125, 127 disposed inwardly of the outer leaves 105, 107. This fixed relationship between the distal section 101 and the proximal section 121 can be accomplished by bonding alternatively the outer cylinder 123 of the proximal section 121 can be provided with a pair of snap flanges 145 which are configured to seat in the windows 129.

The outer leaves 105 and 107 are separated by a radial slot 141 which permits these leaves to be individually moved in opposite directions as the instrument 26 is inserted. In a similar manner, the inner leaves 125 and 127 are separated by a radial slot 143 which is disposed transverse, perpendicular in a preferred embodiment, to the slot 141.

The seal protector 81 is preferably molded from a strong, tough material. In a particular embodiment, characteristics facilitating formation of a living hinge or a lubricious surface may also be of interest. Based on these considerations, materials such as high density polyethylene, Hytrel (a trademark of DuPont), and Valox (a trademark of General Electric) might be considered. The Valox material was chosen for a preferred embodiment.

Depending on the flexibility of the respective leaves 105, 107, 125, and 127, it may be desirable to extend the respective slots 141 and 143 circumferentially along the line which joins the respective leaf to its associated cylinder 103, 123. In FIG. 9 an extension of the slot 141 is designated by the reference numeral 147; an extension of the slot 143 is designated by the reference numeral 149. With the provision of these circumferential slot extensions 147, 149, the leaves 105, 107 and 125, 127 are free to pivot on the remainder of the circumferential structure which functions as a living hinge.

These living hinges are best illustrated in FIG. 11 and designated by the reference numerals 152 and 154 for the respective leaves 105 and 107. This end view of FIG. 11 also illustrates the configuration of the seal protector 81 with the instrument 26 inserted. The accommodating separation of the respective leaves 105, 107 and 125, 127 is apparent from this view.

The seal protector 81 disclosed in these FIGS. 9-11 is illustrated in FIG. 6 mounted to the proximal end of the trocar 10. As illustrated, the protector 81 is preferably mounted co-axially with the aperture 38 with the leaves 105, 107 and 125, 127 functioning as a funnel to guide the instrument 26 toward the aperture 38. In this location, the protector 81 in a preferred embodiment is movable axially between a proximal position, illustrated in FIG. 6, and a distal position illustrated in FIG. 7. These respective positions are defined by interlocking parts of the protector 81 and the annular flange 76 of the end cap 74.

In one embodiment, the cylinder 103 is provided with an annular snap ring having a proximally facing shoulder 158. The cylinder 108 has a distally facing surface 161. In this case, the protector 81 is preferably mounted with the cylinder 103 disposed in sliding engagement with the annular flange 76. The shoulder 158 and surface 161 are separated an axial distance greater than the axial length of the flange 76. This permits the protector 81 to move axially between the proximal and distal positions. In the proximal position, illustrated in FIG. 6, further proximal movement of the protector 81 is prevented by contact between the shoulder 92 on the flange 76 and the shoulder 158 on the cylinder 103. In the distal position, illustrated in FIG. 7, further distal movement of the protector 81 is prevented by contact between the surface 161 of the flange 108 and the surface 94 of the flange 76.

In operation, the instrument 26 is inserted into the funnel formed by the protector 81. As the instrument contacts the inner leaves 125, 127, it moves the protector 81 to the distal position. In this location, the leaves extend between the pointed points 83 of the instrument 26 and the outer portions 39 of the septum valve 36. In a particular embodiment, the distal sections 114, 116 and 132, 136 may actually contact the proximal side of the septum valve 36 although this is not required by the present invention. Nevertheless, this contact is encouraged as it permits the protector 81 to actually engage the septum valve 36. Then as the instrument 26 is further inserted and the leaves 105, 107 and 125, 127 expand radially outwardly, they will also spread the inner portions 37 of the valve 36, thereby enlarging the aperture 38.

Figure 7:
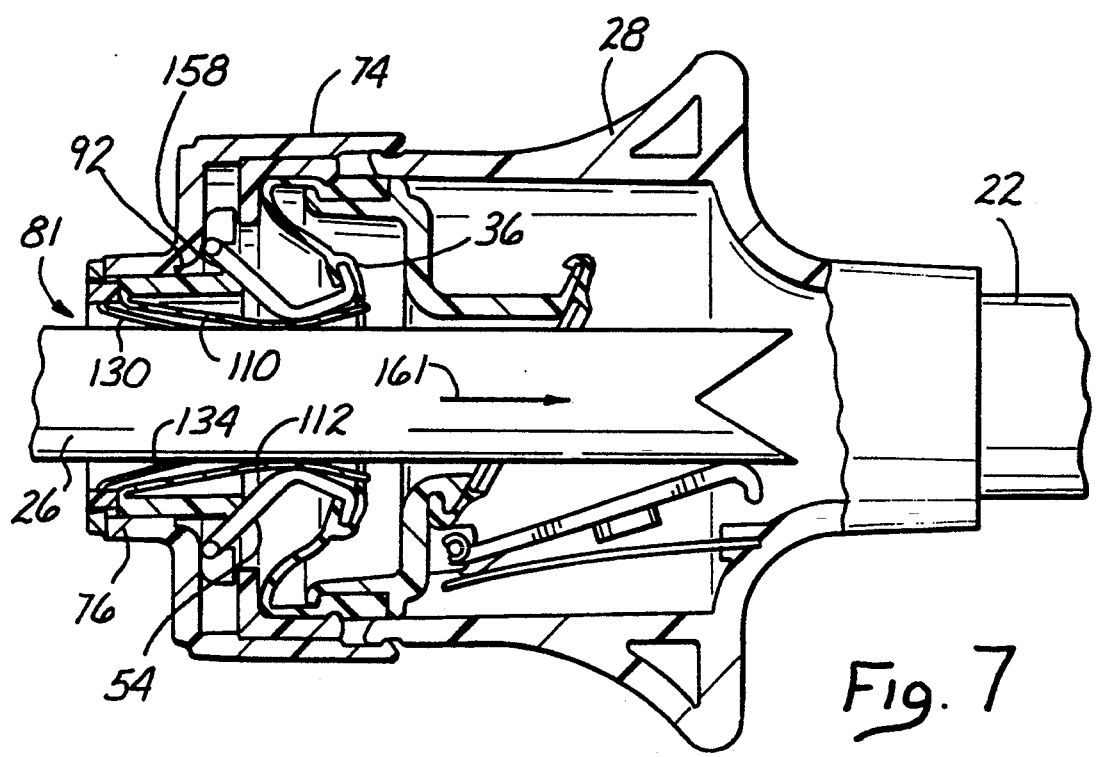
FIG. 7 is an axial cross-section view similar to FIG. 3 illustrating the seal protection mechanism in a distal position as the instrument is being inserted into the trocar.

In the embodiment illustrated in FIG. 7, the distal sections 114, 116 and 132, 136 of the leaves actually extend into the aperture 38 in the distal position. This insures that the aperture 38 is spread at least as far as the leaves of the protector 81. In this case, the protector 81 extends between the instrument 26 and all portions of the septum valve 36.

Once the instrument 26 is in place, it is important that the valve 36 be permitted to engage the outer surface of the instrument in order to form the desired seal and prevent the escape of insufflation gasses. In a particular embodiment, this will require that the seal protector 81 be separated from the septum valve 36 for example by returning the protector 81 to the proximal position.

This movement of the protector 81 from the distal position to the proximal position may occur automatically when the instrument is in place and the protector 81 is no longer subjected to insertion forces. In such an embodiment, the automatic return of the protector 81 would result from the elastomeric forces of the septum valve 36 which compress the leaves 105, 107 and 125, 127 radially inwardly. This compression may result from contact between the valve 36 and the leaves, or contact between the levers 54 and the leaves.

Figure 8:
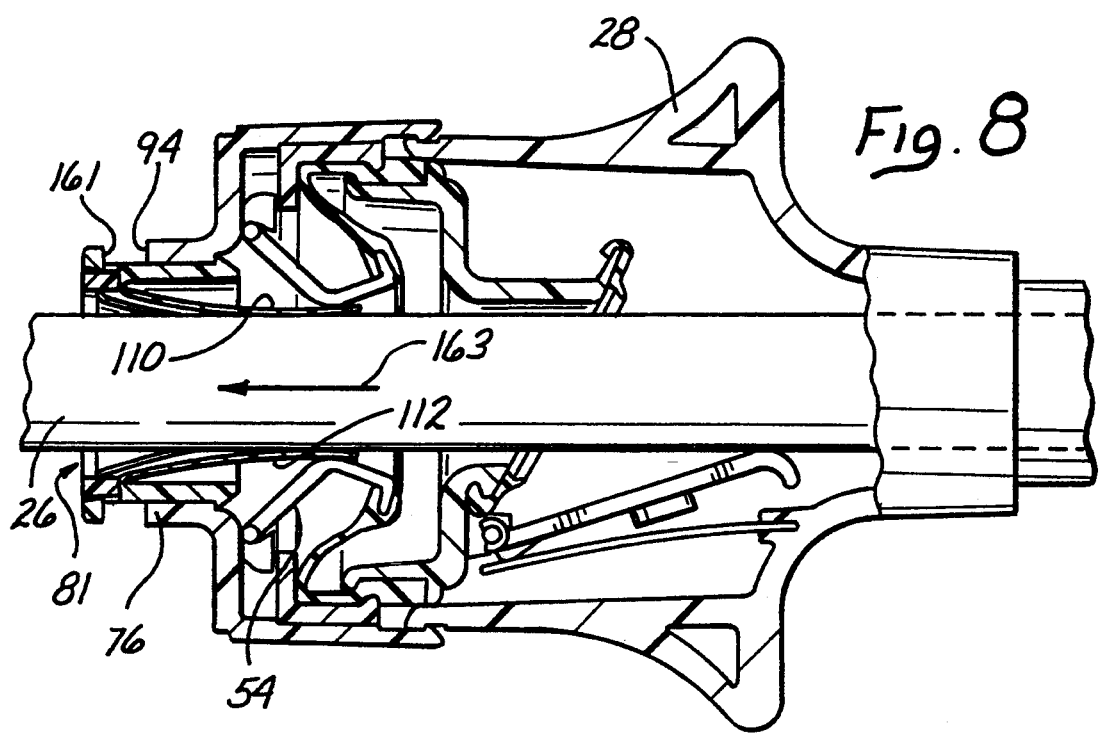
FIG. 8 is an axial cross-section view illustrating the instrument slightly retracted to return the protection mechanism to a proximal position.

In order to facilitate this movement of the protector 81 from the distal position to the proximal position, it may be advantageous to withdraw the instrument 26 slightly to produce a force on the leaves 105, 107 and 125 and 127 in the proximal direction. This movement of the protector 81 to the proximal position is illustrated in FIG. 8 where the feature of automatic retraction is enhanced by the slight movement of the instrument 26 in the direction of arrow 163.

There are many variations on this concept of seal protection which will be apparent to those skilled in the art. Certainly different materials could be used for the protector 81 which could also be formed from more than the two sections 101 and 121. An embodiment including a different number of the leaves 105, 107 and 125, 127 may offer certain advantages in other configurations. It is also particularly advantageous if the protector 81 can protect the valve 36 during insertion of the instrument 26, but also permit the valve 36 to form a seal with the instrument when it has achieved its ultimate position. While these features may be available in an embodiment providing for axial movement of the protector 81, such movement may not be required in other embodiments of the invention.

The septum valve 36, illustrated in FIG. 2 and 3, is of particular interest due to the floating characteristics provided by the outer portion 39. These characteristics are further described with reference to FIG. 12. In this figure both the cannula 22 and the housing 28, are illustrated along with the septum valve 36. The annular lip 40 which defines the central orifice of 38, and the seating portion 46 which circumferentially attaches the septum 36 to the housing 28, are also shown in this view. In the radial cross section of FIG. 12, the letter "A" designates a point on the lip 48 which defines the orifice 38. The reference letter "B" designates a point on the seating portion 46.

The instrument 26 is also illustrated in FIG. 12 but with its axis 170 offset from the normal axis 96 of the orifice 38, as well as the axis 16a of the cannula 22. This offset of the instrument 26 is also shown in the radial cross section view of FIG. 13. From this view it will be apparent that the function of the floating outer portions 39 of the septum 36 is based primarily on the configuration of the septum between the orifice 38 and the seating portion 46. This region is further defined as the region between the reference points "A" and "B" in the axial view of FIG. 12, and the region A–B between the reference circles "A" and "B" in the radial view of FIG. 13.

Within this region A–B, the outer portions 39 have a resiliency which is reduced relative to that of the inner portions 37. In general this means that the outer portions 39 offer less resistance to movement in a radial direction than do the inner portions 37 which define the orifice 38. As a practical matter, this difference in the resiliency of the inner portions 37 and the outer portions 39 means that an instrument, such as the instrument 26, which is inserted off-axis as illustrated in FIGS. 12 and 13, will tend to deflect the outer portions 39 before it deflects the inner portions 37. In a particular embodiment, the reduced resiliency of the outer portions 39 may be characterized as a higher elasticity or higher flexibility than that of the inner portions 37. The result to be greatly appreciated is that the inner portions 37 can move off-axis without deforming the orifice 38. In this off-axis location, the orifice 38 maintains its generally circular configuration without producing the "cat-eye" effect which would result otherwise in a leak between the instrument 26 and the septum 36.

As used herein the term "off-axis" when applied to the instrument 26, means that the axis 94 of the instrument 26 is removed from the axis 16 of the cannula 22. When the term is applied to the septum 36, it means that the axis 96 of the orifice 38 is removed from the axis 16a of the cannula 22.

The region A–B, which has a reduced resiliency relative to the lip 40, can be embodied in many different forms. For example, the septum 36 can be formed with different rings of material, one ring for the inner portions 37 and another ring for the outer portions 39. In such an embodiment (not shown) the ring associated with the outer portion 39 can be formed from a material having increased elastomeric properties relative to the material forming the ring of the inner portions 37.

In the form illustrated in FIGS. 12 and 13, the reduced resiliency of the outer portion 39 is provided by an excess of material between the circles "A" and "B". This excess of material enables the inner portions 37 to easily move off axis without deforming the associated orifice 38.

This excess of material in the region A–B can best be defined with reference to FIG. 12. In this figure, the excess of material in the region A–B is illustrated by the septum 36a having a radial length between the reference points "A" and "B", which is greater than the radial distance between the points "A" and "B". When there is an excess of material, the ratio of this radial length to radial distance is greater than one. While this excess of material will generally be disposed in a uniform circular configuration around the orifice 38, the reduced resiliency could vary around the circumference of the septum 36 in order to encourage off-axis movement of the orifice 38a in a particular direction.

In a further embodiment, the region A–B of reduced resiliency could also be formed by a reduction in the thickness of the septum 36a. With a reduced thickness of material, the region A–B would be more easily stretched than the inner portion 37. The same effect would result, namely the inner portion 37 would move off-axis without significantly deforming the orifice 38.

As the orifice 38 moves off-axis as illustrated in FIG. 14, the region A–B of reduced resiliency functions in two manners. That portion of the region A–B which is disposed in the direction of orifice movement, shown by an arrow 180, is placed in compression. In an embodiment providing an excess of material, this compression at the arrow 180 tends to gather the material thereby offering no resistance to the movement of the orifice 38. At the same time, that portion of the region A–B which is disposed away from the direction of orifice movement, shown by an arrow 182, is placed in tension. In an embodiment providing an excess of material, this tension at the arrow 182 merely tends to unfold the material thereby offering substantially no resistance to movement of the inner portions 37 and the associated orifice 38.

The concept of a floating seal is also included in the embodiment of FIG. 6. In this case, the levers 54 which actuate the septum valve 36 are pivotally attached to a floating ring 184 at the pivots 58. This ring 184 has a diameter which is less than that of an annular recess 186 within which it is free to float.

If the instrument 26 is inserted off-axis, as illustrated in FIG. 12, it contacts the side of the seal protector 81 which transfers that off-axis force to the levers 54. Since the levers 54 float with the ring 184, they tend to move off-axis carrying the inner portions 37 of the septum valve 36 with them. This stretches the outer portions 39 which are away from the direction of movement and compresses the outer portions 39 which are in the direction of the movement. During this process, the inner portions 37 which are supported on the tooth members 62 of the levers 54 are entirely isolated from the off-axis, deflection forces. This isolation automatically occurs with the floating characteristics of the ring 180. Again in this embodiment, the resiliency of the outer portions 39 is less than that of the inner portions 37 because of the force isolation provided by the levers 54. This same concept of a floating ring would also be present in an embodiment which did not include the seal protector 81. Thus in the absence of a seal protector 81, the instrument would immediately contact the levers 54 supported on the ring 184 and thereby provide the desired deformation of the outer portions 38 without deforming the inner portions 37.

Again the advantages of a floating septum seal are apparent in these embodiments where an instrument, such as the instrument 26, which is inserted off-axis, is accommodated without deformation of the inner portions 37 which define the orifice 38. As a result, the orifice 38 moves off-axis toward the instrument 26 without deformation. Even in this off-axis position, the orifice 38 maintains a configuration which optimizes the seal characteristics with the instrument without generating the cat-eye effect.

This concept of a floating septum seal can be embodied in many forms all providing for the undeformed movement of the orifice 38 away from the axis 96 of the trocar 10. Several of these embodiments have been disclosed herein, but many others will now be apparent to those skilled in the art. Given these wide variations within the scope of this concept, one is cautioned not to restrict the invention to the embodiments which have been specifically disclosed and illustrated, but rather encouraged to determine the scope of the invention only with reference to the following claims.

We claim:

1. A trocar adapted to form an access channel across a body wall, and configured to receive a surgical instrument, the trocar comprising:
   a cannula having an axis extending between a proximal end and a distal end of the trocar;
   a seal housing disposed at the distal end of the cannula and forming with the cannula the access channel of the trocar;
   a flexible valve disposed relative to the housing and across the access channel, the valve having elastomeric properties for forming a seal with the instrument when the instrument is disposed in the access channel;
   first portions of the valve defining an orifice which is normally concentric with the axis of the cannula, the first portions being sized and configured to receive the instrument and form the seal with an outer surface of the instrument; and
   second portions of the valve disposed circumferentially outwardly of the first portions of the valve for facilitating movement of the orifice from a first position generally concentric with the axis of the cannula to a second position generally removed from the axis of the cannula, in response to insertion of the instrument along a line removed from the axis of the cannula.

2. The trocar recited in claim 1 wherein:
   the first portions of the valve have a first resiliency which tends to deform the orifice when the instrument is inserted off-axis;
   the second portions of the valve have a second resiliency which tends to move the first portions of the valve off-axis in response to the instrument being inserted off-axis; and
   the resiliency of the second portions of the valve being greater than the resiliency of the first portions of the valve so that the orifice tends to move off-axis without substantial deformation, in response to the instrument being inserted off-axis.

3. The trocar recited in claim 1 wherein the first portions of the valve have a first radial length to radial distance ratio;
   the second portions of the valve have a second radial length to radial distance ratio; and
   the second ratio is greater than the first ratio.

4. The trocar recited in claim 3 wherein the second portions of the valve have a bellows configuration.

5. A trocar adapted to form an access channel across a body wall, the channel being sized and configured to receive a surgical instrument having an outer surface and a first axis, the trocar comprising:
   a cannula having a second axis extending between a proximal end and a distal end of the trocar;
   a seal housing disposed at the distal end of the cannula and forming with the cannula the access channel of the trocar;
   a flexible valve disposed relative to the housing and across the access channel, the valve having elastomeric properties for forming a seal with the instrument when the instrument is disposed in the access channel;
   portions of the valve defining an orifice having a third axis which is normally aligned with the second axis of the cannula, the valve portions being sized and configured to receive the instrument and to form the seal with the outer surface of the instrument; and
   means disposed circumferentially outwardly of the valve portion and responsive to the instrument being inserted with the first axis non-aligned with the second axis of the cannula, for moving the valve portions so that the third axis of the orifice is substantially aligned with the first axis of the instrument.

6. The trocar recited in claim 5 wherein the moving means comprises second portions of the valve disposed circumferentially outwardly of the first portions of the valve, the second portions having characteristics for aligning the third axis of the orifice with the second axis of the cannula without substantial deformation of the orifice.

7. The trocar recited in claim 6 further comprising:
   means responsive to the first axis of the instrument being non-aligned with the second axis of the cannula, for moving the valve portions toward a position wherein the third axis of the orifice is aligned with the first axis of the instrument prior to contact between the instrument and the valve.

8. The trocar recited in claim 7 wherein portions of the housing define an annular recess and the trocar further comprises:
   a lever mechanism disposed proximally of the valve and having a fourth axis generally aligned with the third axis of the orifice;
   the lever mechanism being floatingly supported in the annular recess of the housing; whereby
   insertion of the instrument through the lever mechanism substantially aligns the fourth axis of the lever mechanism and the third axis of the orifice with the first axis of the instrument.

9. A method for forming a seal around an instrument introduced off-axis through an access device, includes the steps of:
   providing a valve in the access device, the valve having an axis and including first portions defining an aperture sized and configured to receive the instrument, and second portions having a greater flexibility than the first portions;
   inserting the instrument into the access device;
   contacting the valve with the instrument at a location off-axis relative to the aperture;
   pushing the instrument through the aperture to form the seal around the instrument; and
   during the pushing step deforming the second portions of the valve, without substantially deforming the first portions of the valve to move the aperture into axial alignment with the instrument.

10. The method recited in claim 9 wherein the providing step includes the step of forming the second portions of the valve with an excess of material, and the deforming step includes the step of gathering the excess of material on the side of the instrument away from the aperture to displace the first portions of the valve into axial alignment with the instrument.

11. The method recited in claim 10 wherein the forming step includes the step of forming the second portions of the valve in a bellows configuration.

12. The method recited in claim 10 wherein the providing step includes the steps of:
forming the first portions of the valve with a first elastomeric material;
forming the second portions of the valve with a second elastomeric material having a greater elasticity than the first elastomeric material.

13. The method recited in claim 9 wherein the providing step includes the steps of:
providing the valve in the form of a septum with the first portions defining the aperture and the second portions extending outwardly of the first portions;
providing the first portions with a first thickness;
providing the second portions with a second thickness less than the first thickness in order to increase the flexibility of the second portions relative to the first portions.

14. A trocar adapted to form an access channel across a body wall and configured to receive a surgical instrument, the trocar comprising:
a cannula having an axis;
a housing disposed relative to the cannula and defining with the cannula the access channel of the trocar, the housing having an annular recess with a first diameter;
a ring disposed in the recess and having a second diameter;
a flexible valve disposed relative to the housing and across the access channel, the valve having an orifice and elastomeric properties for forming a seal with the instrument when the instrument is disposed in the access channel;
a plurality of levers connected to the ring and engaging the valve in proximity to the orifice;
the second diameter of the ring being less than the first diameter of the recess so that the ring and levers are free to float radially of the access of the cannula; whereby
movement of the ring and levers cause the orifice to move without substantial deformation from the axis of the cannula.

15. The trocar recited in claim 14 wherein the levers engage the valve outward of the orifice.

16. The trocar recited in claim 15 wherein the levers are pivotally mounted on the ring.

17. The trocar recited in claim 14 wherein the annular recess is defined in a radial plane substantially perpendicular to the axis of the cannula.

18. An access device adapted to form an access channel across a body wall, and configured to receive a surgical instrument in the access channel, the access device comprising:
a cannula having an axis extending between a proximal end and a distal end of the device;
a seal housing disposed at the distal end of the cannula and forming with the cannula the access channel of the device;
a flexible valve disposed relative to the housing and across the access channel, the valve having elastomeric properties for forming a seal with the instrument when the instrument is disposed in the access channel;
portions of the valve defining an orifice which is sized and configured to receive the instrument and to form the seal with an outer surface of the instrument; and
means disposed circumferentially outwardly of the valve portions for supporting the valve portions within the seal housing, the supporting means being movable relative to the housing to permit the valve portions to float relative to the axis of the cannula.

19. The access device recited in claim 18 wherein:
the valve portions are free to float between a first position and a second position; and
the first position of the valve portions is a natural position where the valve portions are located in the absence of the instrument, and the second position is a stretched position where the valve portions are located in the presence of the instrument.

20. The access device recited in claim 19 wherein the natural position of the valve portions is disposed generally laterally of the stretched position of the valve portions.

21. The access device recited in claim 19 wherein:
the instrument has a first axis, the axis of the cannula comprises a second axis, and the orifice of the valve portions define a third axis;
the third axis of the orifice is aligned with the second axis of the cannula when the valve portions are in the first position.

22. The access device recited in claim 18 wherein the valve portions float generally in a plane transverse to the axis of the cannula.

23. An access device adapted to form an access channel across a body wall, and configured to receive a surgical instrument in the access channel, the access device comprising:
a cannula having an axis extending between a proximal end and a distal end of the device;
a seal housing disposed at the distal end of the cannula and forming with the cannula the access channel of the device;
a flexible valve disposed relative to the housing and across the access channel, the valve having elastomeric properties for forming a seal with the instrument when the instrument is disposed in the access channel;
portions of the valve defining an orifice which is sized and configured to receive the instrument and to form the seal with an outer surface of the instrument, the valve portions being located along a normal axis when the instrument is not present in the access channel; and
means for preventing deformation of the valve portions when the instrument is inserted through the valve along an axis displaced from the normal axis of the valve portions.

24. The access device recited in claim 23 wherein the means for preventing deformation of the valve portions includes means for mounting the valve portions relative to the housing and in a floating relationship with the housing to facilitate radial movement of the valve portions without substantial deformation of the valve portions.

25. The access device recited in claim 24 wherein the portions of the valve are first portions of the valve and the mounting means includes second portions of the valve having a fixed relationship with the valve housing and forming a seal with the valve housing across the access channel.

* * * * *

UNITED STATES PATENT AND TRADEMARK OFFICE
CERTIFICATE OF CORRECTION

PATENT NO. : 5,385,553
DATED : January 31, 1995
INVENTOR(S) : Charles C. Hart et al.

It is certified that error appears in the above-indentified patent and that said Letters Patent is hereby corrected as shown below:

In column 11, line 23, delete the word "distal" and insert therefor --proximal--.
In column 12, line 3, delete the word "distal" and insert therefor --proximal--.
In column 13, line 61, delete the word "distal" and insert therefor --proximal--.
In column 14, line 38, delete the word "distal" and insert therefor --proximal--.

Signed and Sealed this

Sixth Day of August, 1996

Attest:

BRUCE LEHMAN

*Attesting Officer*  *Commissioner of Patents and Trademarks*